United States Patent
Kouyoumjian et al.

(10) Patent No.: US 9,327,082 B2
(45) Date of Patent: May 3, 2016

(54) MEDICATED MODULE FOR USE WITH AUTO-INJECTOR DELIVERY DEVICE

(75) Inventors: Garen Kouyoumjian, Warwickshire (GB); Malcolm Stanley Boyd, Warwickshire (GB); Daniel Thomas De Sausmarez Lintell, Warwickshire (GB)

(73) Assignee: Sanofi-Aventis Deutschland, Frankfurt am Main ( * ) Notice: Subject to any disclaimer, the term of this patent is extended or adjusted under 35 U.S.C. 154(b) by 276 days.

(21) Appl. No.: 13/988,494

(22) PCT Filed: Nov. 28, 2011

(86) PCT No.: PCT/EP2011/071128
§ 371 (c)(1),
(2), (4) Date: May 20, 2013

(87) PCT Pub. No.: WO2012/072552
PCT Pub. Date: Jun. 7, 2012

(65) Prior Publication Data
US 2013/0245561 A1  Sep. 19, 2013

Related U.S. Application Data

(60) Provisional application No. 61/433,826, filed on Jan. 18, 2011.

(30) Foreign Application Priority Data

Nov. 29, 2010 (EP) ..................................... 10192983

(51) Int. Cl.
*A61M 5/315* (2006.01)
*A61M 5/20* (2006.01)
(Continued)

(52) U.S. Cl.
CPC .............. *A61M 5/31596* (2013.01); *A61M 5/20* (2013.01); *A61M 5/2448* (2013.01); *A61M 5/326* (2013.01);
(Continued)

(58) Field of Classification Search
CPC .......... A61M 5/31596; A61M 5/1407–5/1408; A61M 5/2448; A61M 5/2466; A61M 5/31553; A61M 5/31583; A61M 5/347; A61M 5/2066
See application file for complete search history.

(56) References Cited

U.S. PATENT DOCUMENTS 5,102,388 A * 4/1992 Richmond ..................... 604/88
5,104,380 A   4/1992 Holman et al.
(Continued)

FOREIGN PATENT DOCUMENTS

DE   19930631 A1  11/2001
WO      0176665 A1  10/2001
(Continued)

OTHER PUBLICATIONS

Machine Translation of DE19930631.
(Continued)

*Primary Examiner* — Laura Bouchelle
*Assistant Examiner* — Melissa A Snyder
(74) *Attorney, Agent, or Firm* — McDonnell Boehnen Hulbert & Berghoff LLP

(57) ABSTRACT

A drug delivery system to deliver two or more medicaments operable through a auto-injector drug delivery device and a single dispense interface. The device comprises a housing defining a primary reservoir containing a first medicament. A dosing mechanism operably connected to the primary reservoir. A single dispense interface is configured for fluid communication with the primary reservoir and a secondary reservoir of medicament containing at least one drug agent configured for fluid communication to the single dispense interface. A single activation of the dosing mechanism causes medicament from the primary reservoir and a non-user settable dose of the second medicament to be expelled through the single dispense interface.

12 Claims, 7 Drawing Sheets

(51) Int. Cl.
*A61M 5/24* (2006.01)
*A61M 5/32* (2006.01)
*A61M 5/31* (2006.01)
*A61M 5/34* (2006.01)
*A61M 5/178* (2006.01)

(52) U.S. Cl.
CPC ........... *A61M 5/3294* (2013.01); *A61M 5/2066* (2013.01); *A61M 5/2466* (2013.01); *A61M 5/3146* (2013.01); *A61M 5/31553* (2013.01); *A61M 5/31583* (2013.01); *A61M 5/3272* (2013.01); *A61M 5/347* (2013.01); *A61M 2005/1787* (2013.01); *A61M 2005/3247* (2013.01); *A61M 2005/3267* (2013.01); *A61M 2205/581* (2013.01); *A61M 2205/584* (2013.01); *A61M 2205/6045* (2013.01)

(56) References Cited

U.S. PATENT DOCUMENTS

| | | |
|---|---|---|
| 6,562,002 B1 | 5/2003 | Taylor |
| 8,556,862 B2 * | 10/2013 | Cronenberg et al. ......... 604/195 |
| 2006/0276755 A1 | 12/2006 | Sullivan et al. |
| 2008/0015519 A1 | 1/2008 | Klint et al. |

FOREIGN PATENT DOCUMENTS

| | | |
|---|---|---|
| WO | 2010019936 A1 | 2/2010 |
| WO | 2010033795 A2 | 3/2010 |

OTHER PUBLICATIONS

Machine Translation of WO0176665.
Form PCT/IPEA/416, Notification of Transmittal of the International Preliminary Report on Patentability.

* cited by examiner

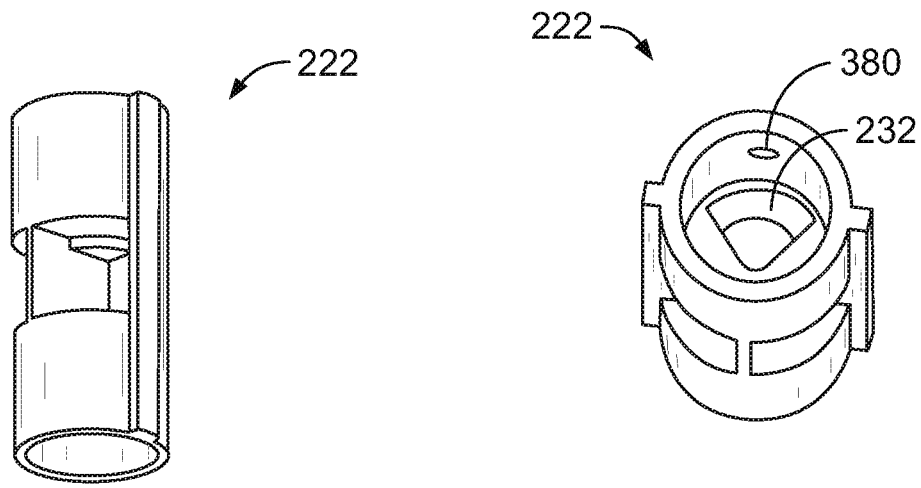
FIG. 11
FIG. 12
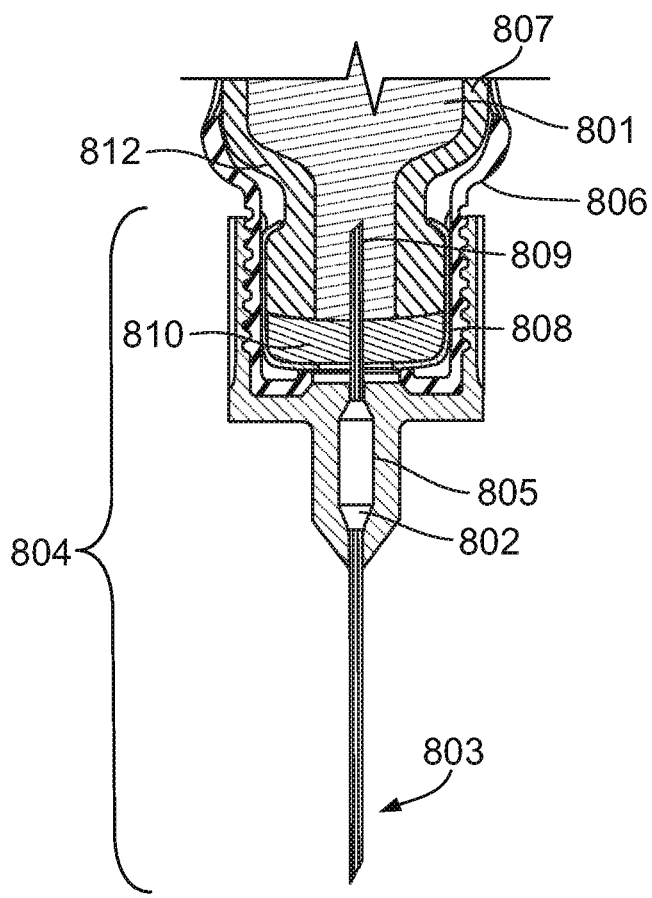
FIG. 13

MEDICATED MODULE FOR USE WITH AUTO-INJECTOR DELIVERY DEVICE

CROSS REFERENCE TO RELATED APPLICATIONS

The present application is a U.S. National Phase Application pursuant to 35 U.S.C. §371 of International Application No. PCT/EP2011/071128 filed Nov. 28, 2011, which claims priority to European Patent Application No. 10192983.4 filed Nov. 29, 2010 and U.S. Provisional Patent Application No. 61/433,826 filed Jan. 18, 2011. The entire disclosure contents of these applications are herewith incorporated by reference into the present application.

FIELD OF INVENTION

The present patent application relates to medical devices and methods of delivering at least two drug agents from separate reservoirs using auto-injection devices comprising a dose setting mechanism and a single dispense interface. Such an auto-injection device may comprise a pen type auto-injection device.

A single delivery procedure initiated by the user causes a non-user settable dose of a second drug agent and a variable dose of a first drug agent to be delivered to the patient. The drug agents may be available in two or more reservoirs, containers or packages, each containing independent (single drug compound) or pre-mixed (co-formulated multiple drug compounds) drug agents. Specifically, our invention concerns a medicated module where the user does not have to manually select or set or manipulate the module to dispense the second drug agent. In one arrangement, where the medicated module comprises a needle guard, activation of the needle guard automatically causes the reservoir of secondary medicament to engage with dispensing conduits to allow a dose of primary medicament and a single fixed dose of the secondary medicament to be injected. In another arrangement, where the medicated module does not comprise a needle guard, activation of a dosing mechanism causes a dose of a primary medicament and a single fixed dose of the secondary medicament to be administered. The disclosed arrangements may be of particular benefit where the therapeutic response can be optimized for a specific target patient group, through control and definition of the therapeutic profile.

BACKGROUND

Certain disease states require treatment using one or more different medicaments. Some drug compounds need to be delivered in a specific relationship with each other in order to deliver the optimum therapeutic dose. This invention is of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems that can arise when delivering two medicaments or active agents simultaneously. The two active agents may interact with each other during the long-term, shelf life storage of the formulation. Therefore, it is advantageous to store the active components separately and only combine them at the point of delivery, e.g. injection, needle-less injection, pumps, or inhalation. However, the process for combining the two agents needs to be simple and convenient for the user to perform reliably, repeatedly, and safely.

A further problem is that the quantities and/or proportions of each active agent making up the combination therapy may need to be varied for each user or at different stages of their therapy. For example one or more active agents may require a titration period to gradually introduce a patient up to a "maintenance" dose. A further example would be if one active agent requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional problems can arise where a multi-drug compound therapy is required, because many users cannot cope with having to use more than one drug delivery system or make the necessary accurate calculation of the required dose combination. This is especially true for users with dexterity or computational difficulties. In some circumstances it is also necessary to perform a priming procedure of the device and/or needle cannulae before dispensing the medicaments. Likewise, in some situations, it may be necessary to bypass one drug compound and to dispense only a single medicament from a separate reservoir.

Accordingly, there exists a strong need to provide devices and methods for the delivery of two or more medicaments in a single injection or delivery step that is simple for the user to perform. The present system and methods can overcome the above-mentioned problems by providing separate storage containers for two or more active drug agents that are then only combined and/or delivered to the patient during a single delivery procedure. Administering a dose of one medicament automatically administers a fixed or determined dose of the second medicament (i.e., non-user settable). The disclosed systems and methods also give the opportunity for varying the quantity of one or both medicaments. For example, one fluid quantity can be varied by changing the properties of the injection by varying or changing the device's "fixed" dose of the secondary drug package. As just one example, the second fluid quantity can be changed by manufacturing a variety of secondary drug containing packages with each variant containing a different volume and/or concentration of the second active agent. The user or healthcare professional would then select the most appropriate secondary package or series or combination of series of different packages for a particular treatment regime.

One arrangement of our invention also provides a medicated module that automatically causes the reservoir of secondary medicament to come into fluid communication with the primary medicament upon activation of the needle guard. This eliminates the need for the user to manually set or adjust the medicated module after performing a priming step. Alternatively, a medicated module for use with an auto-injection delivery device may be provided without a needle guard. By auto-injection delivery device it is meant that such a delivery device utilizes a stored energy source (e.g., a biasing element such as a torsional spring, a motorized power transmission, stored pressure, compression spring, combustion) so as to administer the set dose whereby the energy required to administer the dose is not supplied by the user at the time of dispense. This may be because the user provides the energy to charge the stored energy source prior to administering the dose (e.g. winding a spring against a ratchet) or because the device is supplied with sufficient energy stored within it to power the mechanism for the life of the device (e.g. electrical battery, pressurized gas cartridge, pre-wound spring) and there is therefore no requirement for the user to supply any additional energy other than to trigger the release of the stored energy.

These and other advantages will become evident from the following more detailed description of the invention.

SUMMARY

Our invention allows complex combinations of multiple drug compounds within a single drug delivery system. The invention allows the user to use an auto-injector delivery device (e.g., a pen type auto-injector) and dispense a multi-drug compound device through a single dispense interface. This auto-injector drug delivery device controls the mechanism of the device such that a predefined combination of the individual drug compound may be delivered when a single dose of one of the medicaments is set and dispensed through the single dispense interface. The single dispense interface is a single interface used for dispensing.

By defining the therapeutic relationship between the individual drug compounds, the proposed auto-injector delivery devices and systems could help ensure that a patient/user receives the optimum therapeutic combination dose from a multi-drug compound device without the inherent risks associated with multiple inputs where the user has to calculate and set the correct dose combination every time they use the device. The medicaments can be fluids, defined herein as liquids, gases or powders that are capable of flowing and that change shape at a steady rate when acted upon by a force tending to change its shape. Alternatively, one of the medicaments may be a solid that is carried, solubilized or otherwise dispensed with another fluid medicament.

Accordingly, one specific aspect of particular benefit to users with dexterity or computational difficulties is that the single input and associated predefined therapeutic profile removes the need for a user to calculate their prescribed dose every time they use the device and the single input allows considerably easier setting and dispensing of the combined compounds.

In one preferred embodiment, a master or primary drug compound, such as insulin, contained within a auto-injection delivery device (e.g., a pen type auto-injector) could be used with a single use, user replaceable, medicated module that contains a single dose of a secondary medicament and the single dispense interface (e.g., an injection needle). When connected to the primary device, the secondary compound is activated/delivered on dispense of the primary compound. Although our invention specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with our invention.

For example, the purposes of our invention the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu- Lys-Asn-Gly-Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val- Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

In one preferred arrangement, Applicants' medicated module comprises a needle guard. In one such needle guard arrangement, there is provided a medicated module attachable to the auto-injection delivery device that comprises an outer housing having a proximal end, a distal end, and an outer surface, where the proximal end preferably has a hub holding a double-ended needle and having a connector configured for attachment to the delivery device. There is a reservoir in a bypass housing within the outer housing that contains a medicament. The medicated module assembly may contain a needle guard that can reduce the risk of accidental needle sticks before and after use, reduce the anxiety of users suffering from needle phobia as well as preventing a user from using the device a subsequent time when the additional medicament has already been expelled.

The needle guard is preferably configured with a solid planar surface at its distal end that provides a large surface area that reduces the pressure exerted on the patient's skin, which allows the user to experience an apparent reduction in the force exerted against the skin. Preferably, the planar surface covers the entire distal end of the guard with the exception of a small needle pass through hole aligned axially with the needle. This pass through hole is preferably no more than 10 times greater in diameter than the outer diameter of the needle cannula. For example, with a needle outside diameter of 0.34 mm, the pass through hole diameter D can be 4 mm. Preferably, the pass through hole size should be large enough for the user to see that the device is primed (i.e., a drop or more of medicament) while not being so large that it is still possible to reach the end of the needle with a finger (i.e. needle stick injuries before or after use). This difference between the hole size and cannula diameter is to allow for tolerances, to allow users to see the drop of liquid on the end of the cannula after priming (whether a transparent or non-transparent guard is used) while keeping the size small enough to prevent accidental needle stick injuries.

Further, the movable needle guard or shield is configured to move axially in both the distal and proximal directions when pressed against and removed from an injection site. When the needle assembly is removed or withdrawn from the patient, the guard is returned to post-use extended position. A drive tooth on the inside surface of the guard engages a stop on a track on the outer surface of the bypass housing to securely lock the guard from further substantial axial movement. Preferably a lock out boss on the outer surface of the bypass housing is configured to engage a lock out feature on the inner proximal surface of the outer housing at the completion of the injection to further lock the medicated module from any further use and prevent the needle(s) and/or bypass component from being able to substantially move within the system even if the guard is held in an axially locked condition. By "substantial" movement we do not mean the typical amount of "play" in a system, but instead we mean that the guard and/or distal needle do not move axially a distance that exposes the distal end of the cannula once it is locked out.

One goal of our invention is to eliminate the need to have the user manually operate the medicated module to change the state of the module from a priming state to a combination dose delivery state. Manually operated devices are sometimes not as intuitive as they could be and raise the risk of accidental misuse. One arrangement of Applicants' proposed medicated module solves this problem by utilizing energy stored within the module prior to delivery of the device to the user. The stored energy can come from a biasing member, such as a compressed spring. This stored energy is released during normal user operation of the module by actuating the mechanism and thus activating the state change from prime dose to combination dose. The mechanism aims to make this actuation imperceptible to the user, consequently making the user experience of the module very similar to that of a standard commercially available and accepted needle or safety needle (i.e., unpack module, attach to a auto-injector delivery device, prime auto-injector delivery device, administer a set dose along with single dose in the module). In this way, the module mechanism aims to reduce the risk of unintentional misuse and to improve usability by replicating an already accepted practice for similar injection methods.

As the module mechanism does not require the user to access external features on the module for the purposes of actuation, the number of components and subsequent module size can be reduced/optimized. These factors make the mechanism ideal for a single-use, high-volume manufacture, and disposable device application. Alternatively, as the actuation is driven by a single energy source, the system lends itself to a resettable actuation mechanism. One embodiment described below is the single use (non-resettable) version. The lower hub is preferably restrained rotationally with regard to the needle guard, but is free to move axially within the needle guard. The needle guard is restrained rotationally with regard to the outer housing, but is free to move axially, between defined constraints, within the outer housing.

The user pressing the distal face of the needle guard against the skin causes axial motion of the needle guard in the proximal direction. This axial motion of the guard causes a rotation of the bypass housing through the engagement and action of an inward-facing drive tooth on the guard as it travels in a drive track having one or more paths, which is located on the outer surface of the bypass housing. After sufficient axial travel of the needle guard, the rotation of the bypass housing brings stand-offs inside the outer housing and at the proximal ends of the lower hub into line with pockets located on the outer surface of the bypass housing. Alignment of the stand-offs with the pockets allows the bypass housing to move axially in the proximal direction and further into the outer housing. The lower hub containing a double-ended needle cannula moves axially further onto the bypass housing. Both of these movements occur due to the relaxation/release of the stored energy of the biasing member, preferably a spring that is pre-compressed during module assembly or manufacture, and constitute "triggering" of the actuation mechanism. It is this axial movement of the lower hub onto the bypass housing and the corresponding movement of the bypass housing further into the outer body that results in the double ended needles located in the outer body distal end and the lower hub piercing the medicated module, moving it from a state of priming to combination dose delivery.

Further axial movement of the needle guard is required in order to pierce the skin, this retraction of the needle guard temporarily re-compresses the biasing member creating additional stored energy. At a "commit" point, the proximal axial movement of the drive tooth passes a non-return feature in the track through further rotation of the bypass housing. In normal use, once the drug has been dispensed and the needle is removed from the skin, the needle guard is allowed to return axially in the distal direction under the relaxation of the biasing member as it releases its stored energy. At some point along its return travel, the drive tooth contacts a further ramped face in one of the paths of the track, resulting in yet further rotation of the bypass housing. At this point, the outer housing stand-off comes into contact with a ramp feature on the outer surface of the bypass housing. The combination of this feature with the ramp between the drive tooth and the bypass housing track results in further biasing of the bypass housing stop face into the needle guard drive tooth. The stop face features act as an axial locking pocket. The action of the combined biasing force means that any axial load in the proximal direction put on the needle guard will result in the tooth being stopped in this pocket, locking out the needle guard from further use or exposing the needle. Should the user remove the device from the skin without dispensing fluid, but after the "commit" point has been passed, the needle guard would return to an extended position and lock out as previously described.

In one embodiment, there is provided a medicated module assembly attachable to an auto-injector delivery device, preferably a pen type auto-injector drug delivery device, where the medicated module assembly comprises an outer housing having a proximal end and a distal end, where the proximal end has an upper hub holding a first double-ended needle cannula and a connector configured for attachment to the drug delivery device. The hub can be a separate part from the housing or integral, for example molded as part of the housing. The connector can be any connector design, such as threads, snap fits, bayonet, lure lock, or combination of these designs.

Two needle cannula may be used, a distal cannula and a proximal cannula, with both the distal and proximal cannula preferably being doubled-ended for piercing a septum or seal provided by a cartridge or ampoule contained within the auto-injector delivery device and for piercing in injection site, such as a patient's skin. The distal needle is mounted in a lower hub and the proximal needle is mounted in the upper hub, each using techniques generally known to those skilled in the art, such as welding, gluing, friction fit, over-molding and other like or similar types of techniques. The medicated module assembly also contains a biasing member, preferably a compression spring. The biasing member is preferably in a pre-compressed state and positioned between the proximal inner face of the needle guard and the distal face of the lower hub. Although a preferred biasing member is a spring, any type of member that produces a biasing force will work.

The medicated module assembly automatically, once triggered, changes state from (1) a pre-use or priming state, where a small amount of primary medicament flows in a bypass around the reservoir containing a single dose of the secondary medicament, to (2) a ready-to-use or combination dose state, where both the upper cannula and lower cannula are in fluidic engagement with the fixed dose of the second medicament within the module and where a set dose of the primary medicament can be injected along with the non-settable single dose of secondary medicament in the reservoir, and finally to (3) a locked out state, where the needle guard is prevented from substantial proximal movement. The outer housing preferably has a window or indicator that shows the various states of the module. The indicator can be a pip, knob, button, or the like that protrudes through the outer surface of the proximal end of the needle guard and visually shows the user whether the module is in the pre-use or ready-to-use state. It may also be a visual indicator, e.g. showing colors or symbols, or a tactile or audible indicator. Preferably, user noticeable indicia indicate both a pre-use priming position and a locked position of the guard after the medicated module assembly has been used to perform an injection.

Inside the bypass housing there is a cavity that contains the capsule, which comprises the single dose of medicament in the reservoir. As the needle guard is retracted during an injection, the bypass housing is moved proximally along with the capsule positioned inside the cavity, thus decreasing the cavity volume. This allows the seals of the capsule to be pierced at its top and bottom by the needle cannula such that the medicament can be expelled from the reservoir during dose delivery. When connected to an auto-injector delivery device containing a first medicament and prior to piercing the seals of the reservoir, the needle cannulae are only in fluid communication with the first medicament and a fluid flow path that bypasses the capsule. Preferably, a channel on the inside surface of the bypass housing is part of this fluid flow path and is used in the priming function of the auto-injector delivery device.

As mentioned, the bypass housing preferably has one or more tracks located on the outside surface each having a set of first, second, third, and fourth paths. On the inner surface of the proximal end of the needle guard is one or more radial protrusions or drive teeth. As the guard first begins to retract, these protrusions travel in the first path causing the bypass housing to slightly rotate. As the guard continues to retract and then partially extend, the protrusions travel in the second and third paths. The protrusion moves to the fourth path and into a locking position when the guard is fully extended to its post-use position, which is preferably less extended than the starting position. The guard is rotationally constrained by the outer housing, preferably by the use of one or more spline features in the outer surface of the guard in cooperation with one or more followers or pips located at the distal end of the inner surface of the outer housing. The bypass housing is rotationally constrained when the protrusion is in the second path of the track. As the protrusion is moved axially in the proximal direction when the guard retracts, the protrusion moves from the second track to the third track causing the assembly to emit an audile sound and/or tactile feedback. This tells the user that the device will has now been activated to lock upon extension of the guard in the distal direction. A further aspect of the invention relates to a method of dispensing a fixed dose of one medicament and a variable dose of a primary medicament from separate reservoirs that involves the steps of first attaching a medicated module to and auto-injector delivery device set in a pre-use or prime only state. The user can prime the auto-injector delivery device using only the primary medicament and bypassing the second medicament. After priming the user begins the injection and the needle guard begins to retract and the module automatically changes to second state that allows a combination delivery of the two medicaments. Upon completion of the delivery procedure and retraction of the needle from the injection site, the extension of the needle guard automatically changes the module to a third state.

During dispense, substantially the entire amount of second medicament has been expelled as well as a dose of the first medicament, through the single dispense interface. The capsule preferably contains a flow distributor to ensure that substantially all the single dose of secondary medicament is forced out of the capsule by the primary medicament during an injection. The flow distributor can be a separate stand alone insert or pin. Alternatively the flow distributor and the capsule together can be manufactured or assembled as a one-piece component where the flow distributor is integral with the capsule. Such a unitary construction can be achieved utilizing, for example, design principles such as form fit, force fit or material fit, such as welding, gluing, or the like, or any combination thereof. The one-piece component may comprise one or more medicament flow channels, preferably one flow channel. The capsule and/or flow distributor can be constructed of any material that is compatible to the primary and secondary medicaments. Preferably the capsule and/or flow distributor can be made from compatible materials of construction that include, but are not limited to, COC (an amorphous polymer based on ethylene and norbonene, also referred to as cyclic olefin copolymer, ethylene copolymer, cyclic olefin polymer, or ethylene-norbornene copolymer); LCP (a liquid crystal polymer having an aramid chemical structure that includes linearly substituted aromatic rings linked by amide groups, and further can include partially crystalline aromatic polyesters based on p-hydroxybenzoic acid and related monomers and also highly aromatic polyesters); PBT (polybutylene terephthalate thermoplastic crystalline polymer or polyester); COP (a cyclic olefin polymer based on ring-opening polymerization of norbornene or norbornene-derivatives); HDPE (high density polyethylene); and SMMA (styrene methyl methacrylate copolymer based on methyl methacrylate and styrene). A preferred material is one that is typically used to manufacture septa or pistons (bungs) found in multi-dose medicament cartridges, however, any other material that is compatible with the drug could be used, e.g., glass, plastics or specific polymers, for example, TPE (thermo plastic elastomer); LSR (liquid silicone rubber); LDPE (low density polyethylene); and/or any kind of medical grade rubber, natural or synthetic. By "substantially all" we mean that at least about 80% of the second medicament is expelled from the drug delivery device, preferably at least about 90% is expelled. In the third state, preferably the module is locked so as to prevent a second delivery or insertion by means of a locking mechanism as described previously.

The combination of compounds as discrete units or as a mixed unit is delivered to the body via an integral needle. This would provide a combination drug injection system that, from a user's perspective, would be achieved in a manner that very closely matches the currently available injection devices that use standard needles.

Another embodiment of our invention relates to a auto-injector delivery system to deliver two or more medicaments through a single dose setter and a single dispense interface that comprises a housing containing a dosing mechanism comprising a piston rod operably connected to a primary reservoir of medicament containing at least one drug agent. A triggering mechanism is also operably connected to the primary reservoir of medicament. This triggering mechanism can be any type of mechanism that triggers the delivery procedure, where driven mechanically or through a combination of electronics and/or mechanics and/or biasing mechanisms. The button can move or be a touch sensitive virtual button, for example, a touch sensitive screen. Our system has a single dispense interface configured for fluid communication with the primary reservoir and with a secondary reservoir of medicament containing at least one drug agent. The drug dispense interface can be any type of outlet that allows the two or more medicaments to exit the system and be delivered to the patient. Types of interfaces include hollow needles, catheters, atomizers, pneumatic injectors, or needle-less injectors, mouth-pieces, nasal-applicators and the like interfaces.

The medicated module of our invention can be designed for use with any auto-injector with an appropriate compatible interface. However, it may be preferable to design the medicated module in such a way as to limit its use to one exclusive primary auto-injector pen type delivery device (or family of auto-injector pen type delivery devices) through employment of dedicated/coded/exclusive features to prevent attachment of a non-appropriate medicated module to a non-matching auto-injector. In some situations it may be beneficial to ensure that the medicated module is exclusive to one particular type of auto-injector while also permitting the attachment of a standard drug dispense interface to that same particular auto-injector. This would allow the user to deliver a combined therapy when the module is attached, but would also allow delivery of the primary compound independently through a standard drug dispense interface in situations, such as, but not limited to, dose splitting or top-up of the primary compound.

A particular benefit of the presently disclosed auto-injector devices and systems is that the medicated module makes it possible to tailor dose regimes when required, especially where a titration period is necessary for a particular drug. The medicated module could be supplied in a number of titration levels with obvious differentiation features such as, but not limited to, aesthetic design of features or graphics, numbering etc, so that a patient could be instructed to use the supplied medicated module in a specific order to facilitate titration. Alternatively, the prescribing physician may provide the patient with a number of "level one" titration medicated modules and then when these were finished, the physician could then prescribe the next level. A key advantage of this titration program is that the primary device remains constant throughout.

In a preferred embodiment of our invention, the primary auto-injector delivery device is used more than once and therefore is multi-use; however, the auto-injector delivery device may also be a single use disposable device, such as a disposable auto-injector. It is also possible to have a suite of different medicated modules for various conditions that could be prescribed as one-off extra medication to patients already using a standard drug delivery device. Should the patient attempt to reuse a previously used medicated module, a presently disclosed embodiment includes a locking needle guard that is activated after a first predefined travel/retraction of the guard/insertion of the needle. The locked needle guard would alert the patient to this situation and the inability to use the module for a second time. Visual warnings (e.g. change in color and/or warning text/indicia within an indication window on the module once insertion and/or fluid flow has occurred) can also be used. Additionally, tactile feedback (presence or absence of tactile features on the outer surface of the module hub following use) could be used as well.

A further feature of our invention is that both medicaments are delivered via one injection needle and in one injection step. This offers a convenient benefit to the user in terms of reduced user steps compared to administering two separate injections. This convenience benefit may also result in improved compliance with the prescribed therapy, particularly for users who find injections unpleasant or who have computational or dexterity difficulties.

Our invention also covers a method of delivering two medicaments stored in separate primary packages. The medicaments may both be liquid, or alternatively one or more of the medicaments may be a powder, suspension or slurry. In one embodiment the medicated module could be filled with a powdered medicament that is either dissolved or entrained in the primary medicament as it is injected through the medicated module.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 1b illustrates one arrangement of a cartridge or ampoule that may be used with the auto-injector delivery device illustrated in FIG. 1a;

FIG. 11 illustrates one possible embodiment of a reservoir for use with the medicated module illustrated in FIG. 3;

FIG. 12 illustrates one possible embodiment of a flow distributor for use with the medicated module illustrated in FIG. 3; and FIG. 13 illustrates an alternative embodiment of Applicants' medicated module comprising two needles connected to a secondary reservoir attached to an auto-injector delivery device, such as the auto-injector delivery device illustrated in FIG. 1.

DETAILED DESCRIPTION

The present invention administers a fixed predetermined dose of a secondary drug compound (secondary medicament) and a variable dose of a primary or first drug compound through a single output or drug dispense interface. By the user administering a dose of the primary medicament, the user automatically administers the fixed dose of the second medicament, which preferably is a single dose contained in a medicated module/capsule or reservoir having an integral flow distributor. In a preferred embodiment the drug dispense interface is a needle cannula (hollow needle).

Figure 1A:
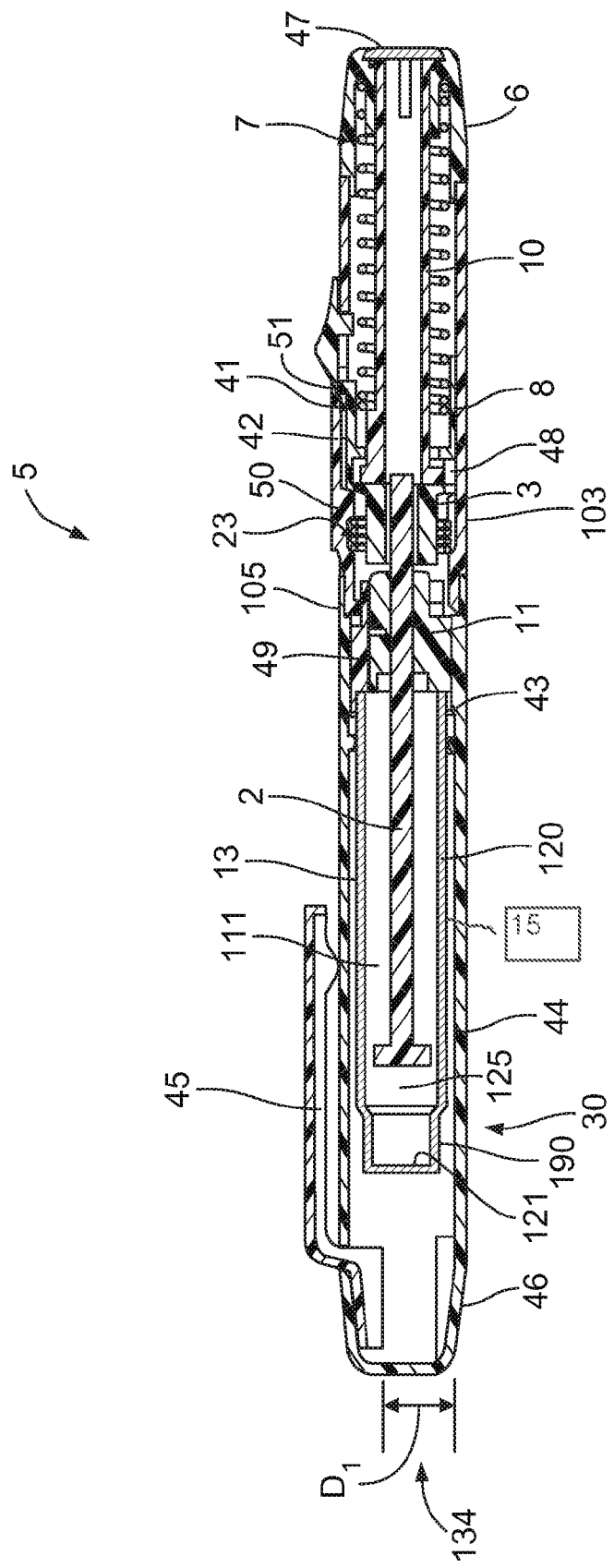
FIG. 1a illustrates one arrangement of an exemplary auto-injector delivery device that can be used with the present invention.

A schematic cross section of one embodiment of the auto-injector delivery device 5 for use with Applicants' medicated modules is illustrated in FIG. 1a. The auto-injector device 5 comprises two main assemblies: dose setting/injecting assembly or body 8 and a cartridge holder 13 for holding a primary reservoir 15, such as an ampoule or cartridge 15. The dose setting assembly 8 and cartridge holder assembly 13 of this auto-injector device are similar in design and operation to that described in U.S. Pat. No. 5,104,380 which is herein entirely incorporated by reference and to which the reader is directed to for further details. Such an auto-injector device 5 may comprise a pen type auto-injector device provided by Owen Mumford Limited of Oxford, England under the tradename of AutoPen.

The auto-injector 5 illustrated in FIG. 1a is just one type of auto-injector delivery device that can be used with Applicants' medicated module 140 (see FIGS. 3-13). This medicated module 140 could be releasably attached to a connection means 190 provided near a distal end 30 of the auto-injector cartridge holder 13. Applicants' medicated module 140 is preferably self-contained and may be provided as a sealed and sterile disposable module that has an attachment means compatible to the attachment means 190 at the distal end 30 of auto-injector device 5. Although not shown, the medicated module 140 could be supplied by a manufacturer in a protective and sterile container, where the user would peel or rip open a seal or the container itself to gain access to the sterile medicated module. In some instances it might be desirable to provide two or more seals for each end of the medicated module.

The auto-injector delivery device 5 is in the form of a pen type auto-injector delivery device. This auto-injector delivery device 5 comprises a dose setting mechanism 8, a cartridge holder 13, and a removable cap 46. The dose setting mechanism 8 further comprises a piston rod 2, such as a threaded piston rod that advances in a distal direction (i.e., towards the injection site) when a previously set dose is to be injected or administered.

A proximal end 105 of the cartridge holder 13 and a distal end 103 of the dose setting mechanism 8 are removably secured together. The auto-injector pen type syringe may comprise a re-usable or a disposable pen type syringe. Where the auto-injector comprises a reusable device, the cartridge holder 13 and the dose setting mechanism 8 are removably coupled together. In a disposable auto-injector device, the cartridge holder 13 and the dose setting mechanism 8 are permanently coupled together.

To inject a previously set dose, a drug dispense interface (e.g., a double ended needle assembly) is attached to the coupling mechanism 190 provided near the distal end 30 of the cartridge holder 13. For example, in one preferred arrangement, the coupling mechanism 190 provided near the distal end 30 of the cartridge holder 13 may comprise a thread 121 (or other suitable connecting mechanism such as a snap lock, snap fit, form fit, or bayonet lock mechanism) so that the drug dispense interface may be removably attached to the distal end of the cartridge holder 13. When the auto-injector delivery device 5 is not in use, the removable cap 46 can be releasably retained over the cartridge holder 13.

Figure 1B:
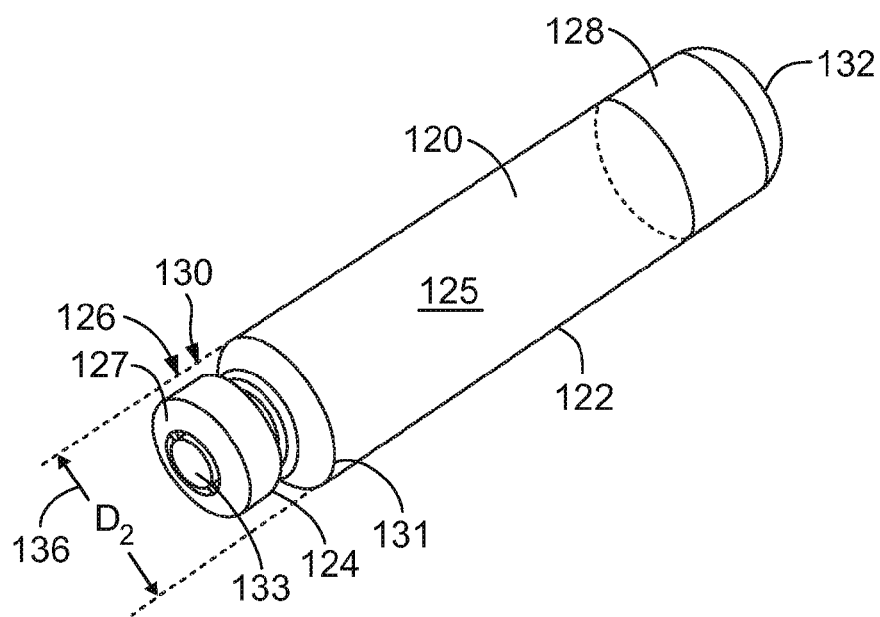

An inner cartridge cavity 111 defined by the cartridge holder 13 is dimensioned and configured to securely receive and retain the ampoule or cartridge 120. FIG. 1b illustrates a perspective view of a cartridge 120 that may be used with the auto-injector delivery device 5 illustrated in FIG. 1a. The cartridge 120 includes a generally tubular barrel 122 extending from a distal end 130 to a proximal end 132. The distal end 130 is defined by an inwardly converging shoulder 131.

At the distal end 130, the cartridge 120 includes a smaller diameter neck 126 and this neck projects distally from the shoulder 131 of the barrel 122. Preferably, this smaller diameter neck 126 is provided with a large diameter annular bead 133 and this bead extends circumferentially thereabout at the extreme distal end of the neck 126. A pierceable seal or septum 127 is securely mounted across the open distal end defined by the neck. The seal 127 may be held in place by a metallic sleeve or ferrule 124. This ferrule 124 may be crimped around the circumferential bead at the distal end of the neck. The medicament 125 is pre-filled into the cartridge 120 and is retained within the cartridge, in part, by the pierceable seal 127, the metallic sleeve 124, and the stopper 128. The stopper 128 is in sliding fluid-tight engagement with the inner tubular wall of the barrel 122. Axially directed forces acting upon the stopper 128 during a dose injection step or dose administration step urges the medication 125 from the cartridge though a double ended needle mounted onto the distal end 30 of the cartridge holder 13 and then into an injection site. For example, if the cartridge 120 is provided in the cartridge holder 13 of auto-injector 5, such axial forces may be provided by the piston rod 2 of the dose setting mechanism 8.

A portion of the cartridge holder 104 defining the cartridge holder cavity 111 is of substantially uniform diameter represented in FIG. 1a by D1 134. This diameter D1 134 is preferably slightly greater than the diameter D2 136 of the cartridge 120. The interior of the cartridge holder 13 includes an inwardly-extending annular portion or stop that is dimensioned to prevent the cartridge 120 from moving within the cartridge holder 13. In this manner, when the cartridge 120 is loaded into the cavity 111 of the cartridge holder 13 and the cartridge holder 13 is then connected to the dose setting member 8, the cartridge 120 will be securely held within the cartridge cavity. More particularly, the neck 126 and ferrule 124 of the cartridge 20 are inserted in a proximal to distal direction into the open proximal end of the cartridge holder 13 with the ferrule eventually passing entirely into the holder 13. With the holder 13 removably coupled to the dose setting mechanism 8, the proximal end of the cartridge 120 may abut a stop provided by the dose setting member 8.

A number of doses of a primary medicament 125 may be dispensed from the cartridge 120. It will be understood that the cartridge 120 may contain a type of medicament that must be administered often, such as one or more times a day. One such medicament is insulin. A movable piston 128 (FIG. 1B) is retained in a first end or proximal end of the cartridge 120 and receives an axial force created by the piston rod 2 of the dose setting mechanism 8.

Returning to FIG. 1a, as illustrated, the dose setting mechanism 8 is closed at its distal end by a piston rod guide 11. This piston rod guide 11 may be clipped into the auto-injector dose setting mechanism 8. Preferably, the device body comprises a cylindrical boss extending in the distal direction and being externally threaded so as to accommodate the cartridge holder 13. The cartridge or ampoule 20 of a primary medicament 125, such as either a short acting or a long acting insulin, is provided into the cartridge holder 13. Where the auto-injector device 5 comprises a reusable device, after the cartridge 20 has been placed within the cartridge holder 13, the holder may be releasably connected onto the boss on the device body. In one preferred arrangement, the holder 13 may comprise a first threaded connection that may be releasably coupled to a second thread connection provided near a distal end of the delivery device body.

The piston rod guide 11 guides longitudinal movement of the piston rod 2 either during a dose administration step or during an auto-injector resetting step. The piston rod guide 11 guides movement of the piston rod 2 from a recess in the end of the plunger guide 11 in a most proximal direction (where the piston rod extends along an inner cavity of the body 8 towards the end cap 47), progressively into the open end of the cartridge 20 as the primary medicament 125 is injected through a dose dispense interface coupled to the distal most end 30 of the cartridge holder 13. In one arrangement, the piston rod guide 11 comprises a bore and this bore has opposed flats for preventing rotation of the piston rod 2 as the piston rod 2 moves into the cartridge 20 during a dose administration step.

With the auto-injector device illustrated in FIG. 1, a dose of the medicament 125 to be administered may be set by first taking off the drug delivery device cap 46. Then, a dispense interface could be connected to the distal end of the cartridge holder.

Importantly, in the auto-injector delivery device 5 illustrated in FIG. 1, movement of the piston rod 2 in the distal direction may be achieved by energy stored in a biasing member 6. Such a biasing element 6 may comprise a helical spring. For example, as a user sets a dose of the primary medicament 125 to be injected by turning the dose dial grip 7 in a clock-wise direction, the biasing member 6 becomes twisted under tension. Therefore, a pre-set dose of the primary medicament 125 to be administered is set by rotation of a dose dial grip 7 which can turn about the proximal end of the dosing mechanism 8. The dose dial grip 7 has a window through which graduations can be read to show the angle through which the cap has been turned.

Once the dispense interface has been properly connected to the distal end of the auto-injector 5, the dose of the primary medicament may be set by turning the dose dial grip 7 about the dose setting mechanism 8. The dose dial grip 7 is fastened to other components of the dose setting mechanism 8 such as an end cap 47, a drive sleeve 10, and one end of the biasing member 6. The other end of the biasing member 6 may be locked to a spring retainer 41. Preferably, this spring retainer 41 fits inside the dose setting member 8 and is keyed against rotation in relation to the setting member 8. Most preferably, this spring retainer 41 is configured to fit inside the dose setting member 8 and can be keyed against rotation in relation to the dose setting member 8 by an external key 51 that is seated in a notch formed along an inner wall surface of member 8.

At a distal end of the drive sleeve 10, an annular flange sites within the proximal end of a drive gear 3 and the flange on the drive sleeve 10 and the drive gear have cooperating ratchet teeth. These ratchet teeth enable the drive sleeve 10 to be turned in one direction only in relation to the drive gear 3. The drive gear 3 is keyed against rotation in the dose setting mechanism 8 by means of a trigger slide 42. The trigger slide 42 is shown in the proximal position shown in FIG. 1. Preferably, the trigger slide 42 has an internal spline 50 that engages an external spline on the drive gear 3. In one preferred arrangement, the drive sleeve 10 comprises a plastics molding formed integrally at the distal end with a circumferentially extending arm having at its free end a radially outwardly extending ratchet tooth, which is urged by the resilience of the arm into engagement with a ring of ratchet teeth on the drive gear 3.

During a dose setting step, when the dose dial grip 7 is rotated, the user can count the clicks as the ratchet tooth moves over successive teeth on the drive gear. In addition, the user can also observe the movement of a scale provided on the dose dial grip 7 in relation to a pointer that may be provided along an outer surface of the body 8. This enables the user to set the preset dose visually as well as aurally.

The auto-injector further comprises a second biasing member 23, in the form of a second spring 23. This second biasing member 23 acts so as to urge the trigger slide 42 in the proximal direction so as to maintain the trigger slide's 42 engagement with the drive gear 3. This engagement prevents the unwinding of the biasing member 6 until the triggering mechanism has been activated, consequently administering the dose.

Once the preferred dose has been set and a dispense interface has been properly attached to the distal end 30 of the cartridge housing 13, the user can push the trigger slide 42 in the distal direction as defined by stops at the end of a slot formed in the dose setting mechanism 8. As this trigger slide 42 is moved in this distal direction towards the injection site, an internal flange on the trigger slide 42 also moves in the distal direction so as to compress the second biasing member/spring 23. Compression of the second biasing element 23 moves the spline out of engagement with the drive gear 3. As such, the drive gear 3 will no longer be retained against rotation, so that the first biasing element 6 can now unwind and thereby rotate the drive sleeve 10 and the drive gear 3.

The piston rod 2 is formed with an integral quick pitch screw thread cooperating with a corresponding internal thread in the bore of the drive gear 3. As such, rotation of the drive gear 3 will cause axial movement of the piston rod 2 in the distal direction. Rotation of the drive gear 3 continues until an external projection on the drive sleeve 10 comes against a stop consisting of an internal projection formed in the spring retainer 41 when the preset dose will have been discharged from the cartridge by the piston rod 2.

The piston rod 2 is prevented from rotation during dose dispense. Preferably, the piston rod 2 is prevented from rotating during dose dispense by two opposed axial flats formed on the piston rod 2 and locating in a correspondingly shaped hole in the piston rod guide 11. This piston rod guide may also acts as a rewind knob. The piston rod guide 11 is normally retained against rotation in the body 8 by a locking bar 49 fitted into an axially extending slot in the piston rod guide 11 and having an external tooth cooperating with an internal tooth at the distal end of the dose setting mechanism 8. In one preferred arrangement, the locking bar 49 comprises a radially inwardly extending piece fitted in a notch in the bottom of the slot and acting as a pivot. When the locking bar is unrestrained, the natural position of its distal end is radially outwardly of the position shown in FIG. 1a so that the tooth at the proximal end is pivoted radially inwardly out of engagement with the corresponding tooth at the distal end of the dose setting mechanism 8. However, when a housing connector 43 is fitted over the piston rod guide 11 and the distal end of the body 8, it deflects the distal end of the piston rod bar 49 radially inwardly to the position shown in FIG. 1a in which the tooth at the proximal end is in engagement with the body 8.

To set a subsequent dose of the primary medicament 125 contained with cartridge 20, the dose dial grip 7 is turned through the desired number of stops after the trigger slide 42 has been moved by the second biasing element 23 back to the proximal position. Then, when the trigger slide 42 is operated yet again, a further dose may be ejected.

Multiple injections may continue until the cartridge is exhausted. Where the auto-injector 5 comprises a non-reusable auto-injector, the user merely disposes of the auto-injector and retrieves a prefilled auto-injector for subsequent injections.

However, where the auto-injector 5 comprises a reusable auto-injector, the cartridge holder 13 may be removed from the dose setting mechanism 8 by unscrewing the housing connector 43. Removing the dose setting mechanism 8 from the holder 13 releases the piston rod guide 11 for rotation in relation to the dose setting mechanism 8. As such, the piston rod guide 11 can now act as a rewind knob. That is, the piston rod guide 11 can be turned by hand to drive the piston rod 2 back in the proximal direction to an initial piston rod starting position. This will allow the user to insert a fresh cartridge into the cartridge holder 13. Then, when the housing connector 43 is re-engaged, the rewind knob is locked in position ready for further operation.

In one arrangement, the proximal end of the piston rod 2 carries a C clip 48. The C clip 48 defines the extreme distal position of the piston rod 2.

Figure 3:
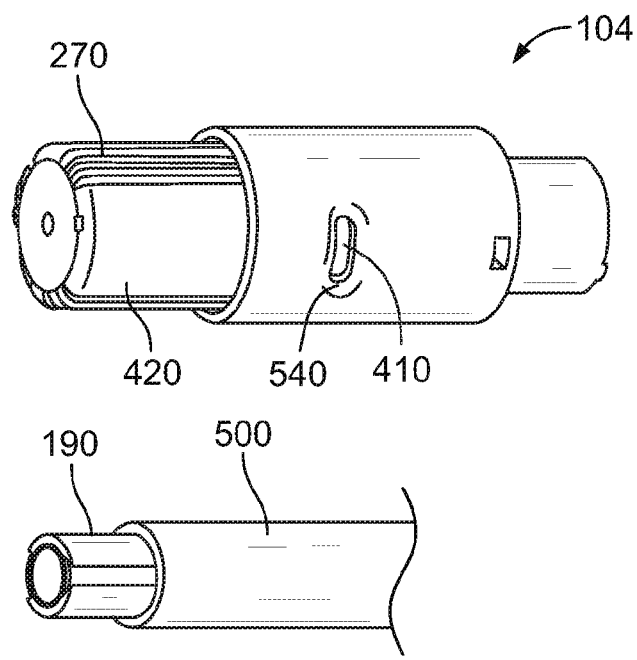
FIG. 3 illustrates an embodiment of a medicated module of the present invention, where the medicated module is separated from a primary reservoir of an auto-injector delivery device, such as the primary reservoir of the auto-injector delivery device illustrated in FIG. 1.

As previously described, the auto-injector 5 comprises a coupling mechanism 190 for releasably coupling a medicated module, such as the medicated module 140 illustrated in FIG. 3. As just one example, in one arrangement, the auto-injector delivery device 5 may include a coupling mechanism 90 in the form of a threaded section 121. This threaded section 121 of the auto-injector 5 threadably couples a corresponding attachment means or connector 180 on the medicated module 140. (See, e.g., FIG. 5). Alternatively, in another auto-injector delivery device arrangement, other known coupling mechanisms 190 can be used to attach the medicated module to the distal end of the drug delivery device. This could include types of permanent and/or removable connection means, such as threads, snap locks, snap fits, luer locks, bayonet, snap rings, keyed slots, and combinations of such connections.

In some situations, however, it may be also beneficial to ensure that the medicated module 140 is exclusive to one type of auto-injector while also permitting the attachment of a standard needle, such as a standard double ended needle assembly that is generally known to those skilled in the art. One advantage of such an arrangement is that such a situation would allow the user to deliver a combined therapy when the medicated needle 140 is attached to the drug delivery device but would also allow the user to deliver a primary compound independently through a standard needle in situations such as, but not limited to, dose splitting or top-up of the primary compound or where the second compound was not required at all. In the latter situation, an auto-injector could be used on its own to deliver the primary medicament. Then, if and when required, the medicated module could be used to deliver a second medicament without the need for two injections. The medicated module could have an exclusive interface such that it can only be used with one such dedicated pre-filled auto-injector for reasons such as safety. A range of medicated modules could contain a variety of medicaments for various situations/scenarios all of which could be delivered in combination with the medicament from the auto-injector (primary device). It is also possible that the auto-injector contains only a buffer solution or dilutant to dispense a concentrated medicament from the medicated module.

Figure 2:
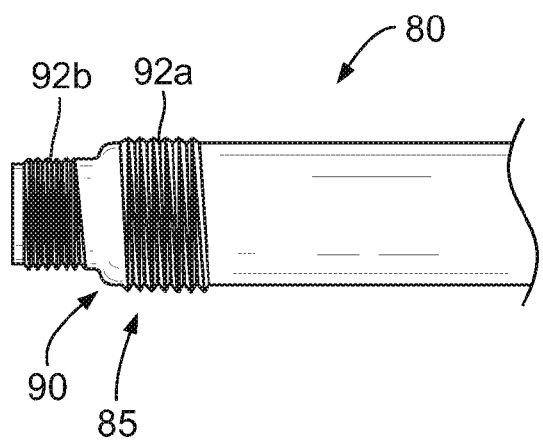
FIG. 2 illustrates one arrangement of a distal end of an auto-injector delivery device, such as the distal end of the auto-injector delivery device illustrated in FIG. 1.
Figure 4:
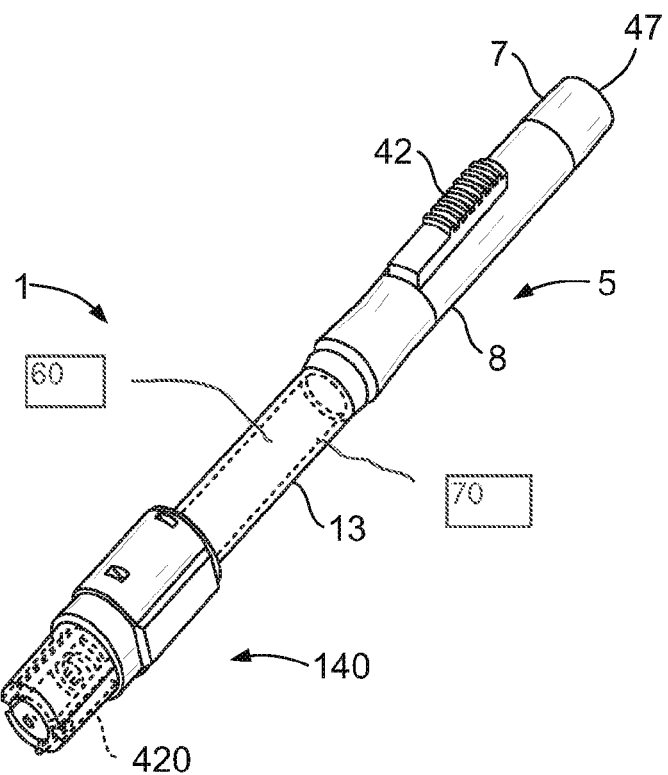
FIG. 4 illustrates the medicated module illustrated in FIG. 3 attached to a distal end of an auto-injector delivery device, such as the auto-injector delivery device illustrated in FIG. 1.

One such exclusive attachment means for achieving the partial exclusive attachment is illustrated in FIG. 3. For example, FIG. 2 illustrates a distal end 85 of an auto-injector delivery device 80, such as the distal end 30 of the auto-injector device 5 illustrated in FIG. 1. As illustrated, the distal end 85 comprises a coupling mechanism 90. This coupling mechanism comprises a first attachment means 92a and a second attachment means 92b. In this illustrated arrangement, both the first and second attachment means 92a, 92b are shown in the form of a first and a second threaded sections. In this example, the first threaded section 92a permits the attachment of a medicated module, such as the medicated module illustrated in FIG. 3. The second threaded section 92b permits the attachment of a standard needle double ended needle assembly. Although only showing threaded interfaces, other coupling mechanisms could also be used for the standard needle section and the means of attaching the medicated needle is not limited to just screw threads. With such a coupling mechanism 90, a medicated module could be releasably coupled to the auto-injector. For example, FIG. 4 illustrates a drug delivery system 1 comprising a medicated module 140 coupled to a distal end of an auto-injector, such as the distal end 30 of the auto-injector 5 illustrated in FIG. 1.

Figure 5:
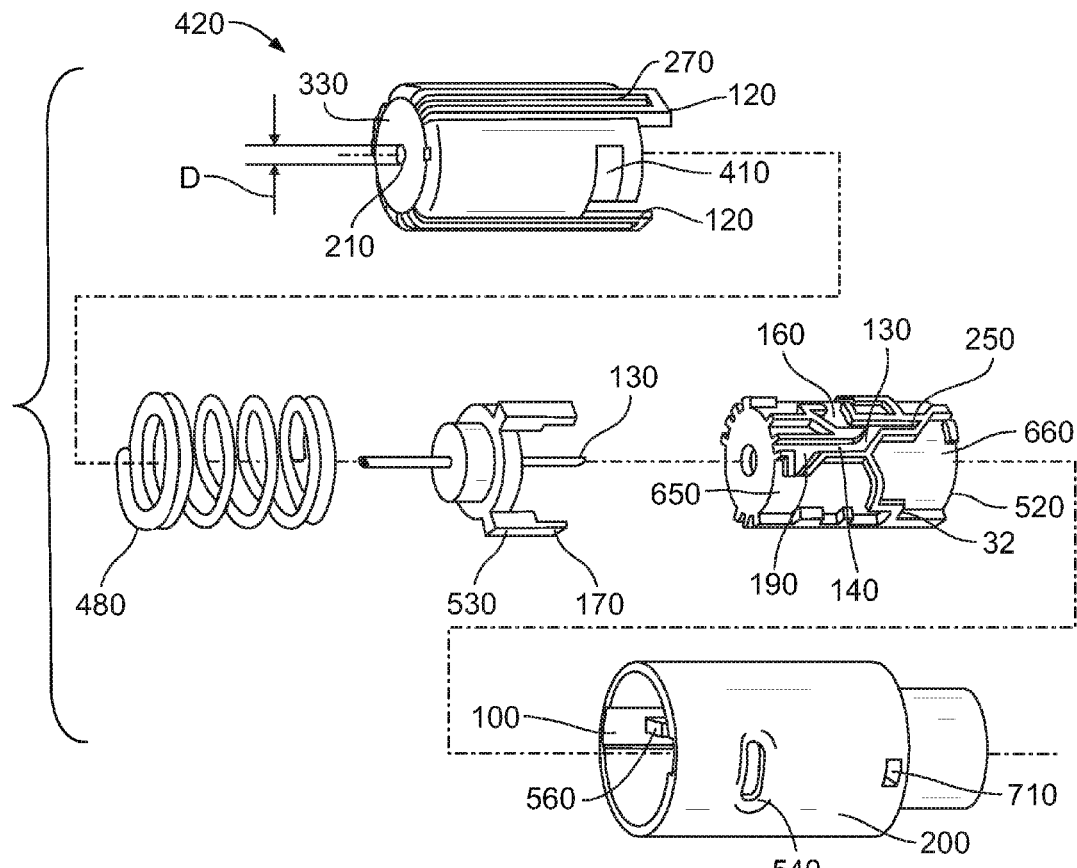
FIG. 5 illustrates an exploded distal perspective view of all the components (except the medicated capsule) of the medicated module illustrated in FIG. 3.
Figure 6:
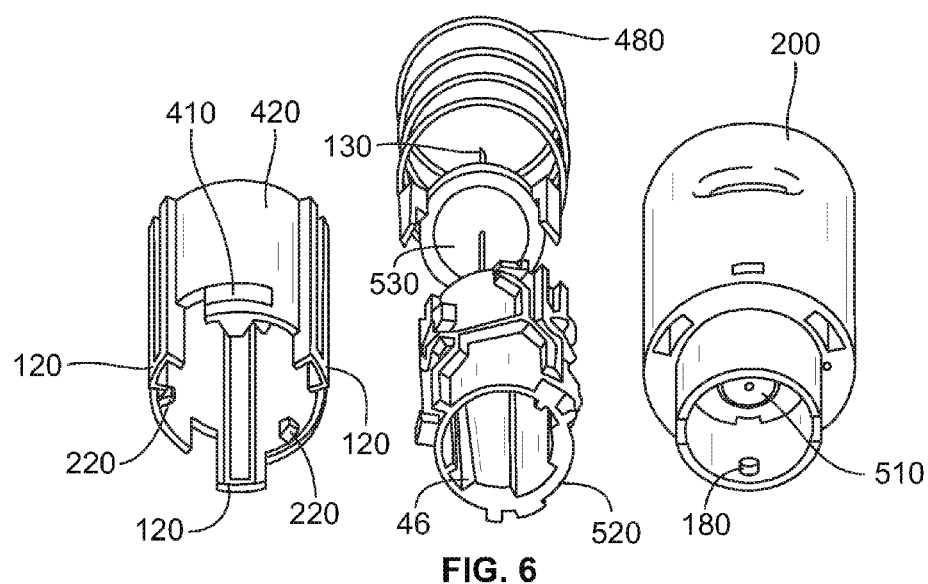
FIG. 6 illustrates an exploded proximal perspective view of all the components (except the medicated capsule) of the medicated module illustrated in FIG. 3.

FIGS. 3-10 illustrate one embodiment of a medicated module comprising a needle guard. For example, FIGS. 3 and 6 illustrate an alternative attachment means 190 of a drug delivery device, such as the auto-injector illustrated in FIG. 1A. As illustrated, this attachment means 190 comprises a unique bayonet type connection that is keyed specifically to a corresponding female bayonet type connection 180 on hub 510 of medicated module 140. These illustrated embodiments have the benefit of the second medicament as a single dose being contained entirely within capsule 310, and specifically in reservoir 222, hence minimizing the risk of material incompatibility between the second medicament and the materials used in the construction of the medicated module 140, specifically housing 200, inner housing 520, or any of the other parts used in the construction of the medicated module.

Figure 7:
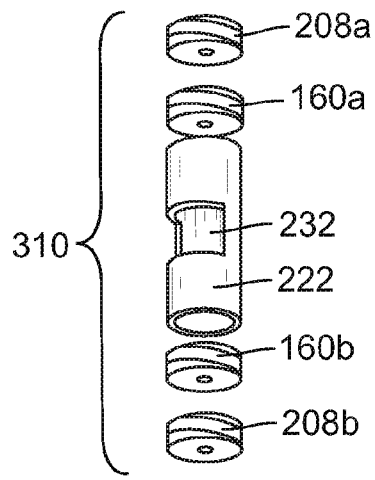
FIG. 7 is a perspective view of the capsule containing the reservoir of the embodiment of FIG. 3.
Figure 8:
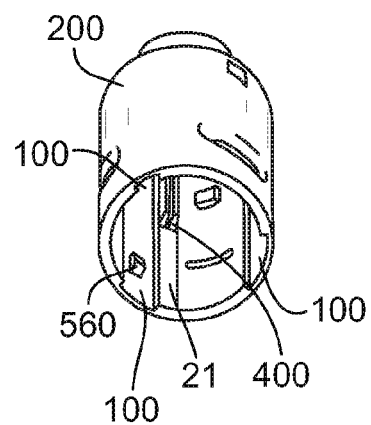
FIG. 8 illustrates a proximal perspective view of the outer housing of the embodiment of FIG. 3.

To minimize the residual volume of the second medicament, caused by recirculation and/or stagnant zones, that might remain in capsule 310 at the end of the dispense operation, it is preferable to have a flow distributor 232 as an integral part of reservoir 222 (see FIG. 7). The reservoir 222 containing the single dose of the secondary medicament can be sealed with septa 160a and 160b, which are fixed to the capsule using keepers or plugs 202a and 202b. Preferably the keepers have fluid channels that are in fluid communication with needles 130 and 150 and with bypass 460, which is preferably part of the inside surface of bypass housing 520. Together this fluid path allows priming of the drug delivery device before injection. Preferably the reservoir, flow distributor, keepers, and bypass can be made from materials that are compatible with the primary medicament. Examples of compatible materials of construction include, but are not limited to, COC (an amorphous polymer based on ethylene and norbonene, also referred to as cyclic olefin copolymer, ethylene copolymer, cyclic olefin polymer, or ethylene-norbornene copolymer); LCP (a liquid crystal polymer having an aramid chemical structure that includes linearly substituted aromatic rings linked by amide groups, and further can include partially crystalline aromatic polyesters based on p-hydroxybenzoic acid and related monomers and also highly aromatic polyesters); PBT (polybutylene terephthalate thermoplastic crystalline polymer or polyester); COP (a cyclic olefin polymer based on ring-opening polymerization of norbornene or norbornene-derivatives); HDPE (high density polyethylene); and SMMA (styrene methyl methacrylate copolymer based on methyl methacrylate and styrene). The needle pierceable septa, bungs, and/or seals that are used with both the capsule and the primary medicament cartridge can be manufactured using TPE (thermo plastic elastomer); LSR (liquid silicone rubber); LDPE (low density polyethylene); and/or any kind of medical grade rubber, natural or synthetic.

The design of flow distributor 232 should ensure that at least about 80% of the second medicament is expelled from reservoir 222 through the distal end of needle 130. Most preferably at least about 90% should be expelled. Ideally, displacement of the first medicament of a primary reservoir contained within a primary device, such as the non-presettable drug delivery device 5, and through the capsule 310 will displace the single dose of the second medicament stored in reservoir 222 without substantial mixing of the two medicaments.

Attachment of the medicated module 140 to the non-settable delivery device 5 causes proximal needle 150 to penetrate a septum sealing the distal end of the cartridge, and hence the primary reservoir 70 containing the primary medicament of the auto-injector delivery device 5. For example, FIG. 4 illustrates the medicated module 140 attached to the auto-injector 5 where a proximal needle of the medicated module 140 pierces a septum of the cartridge contained within the auto-injector 5 so that the proximal needle resides in fluid communication with the primary medicament 60 contained within the primary reservoir 70 of the auto-injector 5.

Once needle 150 of the medicated module 140 has passed through the septum 22 of the primary reservoir 70, fluid connection is made between the first or primary medicament 60 and the needle 150. At this point, the system can be primed by setting a small dose and then triggering the dosing mechanism 10 so that the piston rod 2 moves in the distal direction. As the piston rod 2 acts on the stopper contained within the cartridge, a small number of units of the first medicament 60 contained in the primary reservoir 70 will be expelled from the medicated module.

Once the device 5 is primed, then activation of the needle guard 420 allows dispense of the medicaments by subcutaneously injecting the medicaments via further activation of plunger 30 on device 5. The plunger 30 of the dosing mechanism 10 can comprise any triggering mechanism that causes the dose of the first medicament to move towards the distal end 20 of the device 5. In a preferred embodiment, the dosing button is operably connected to a plunger that engages a piston in the primary reservoir of the first medicament.

Figure 9:
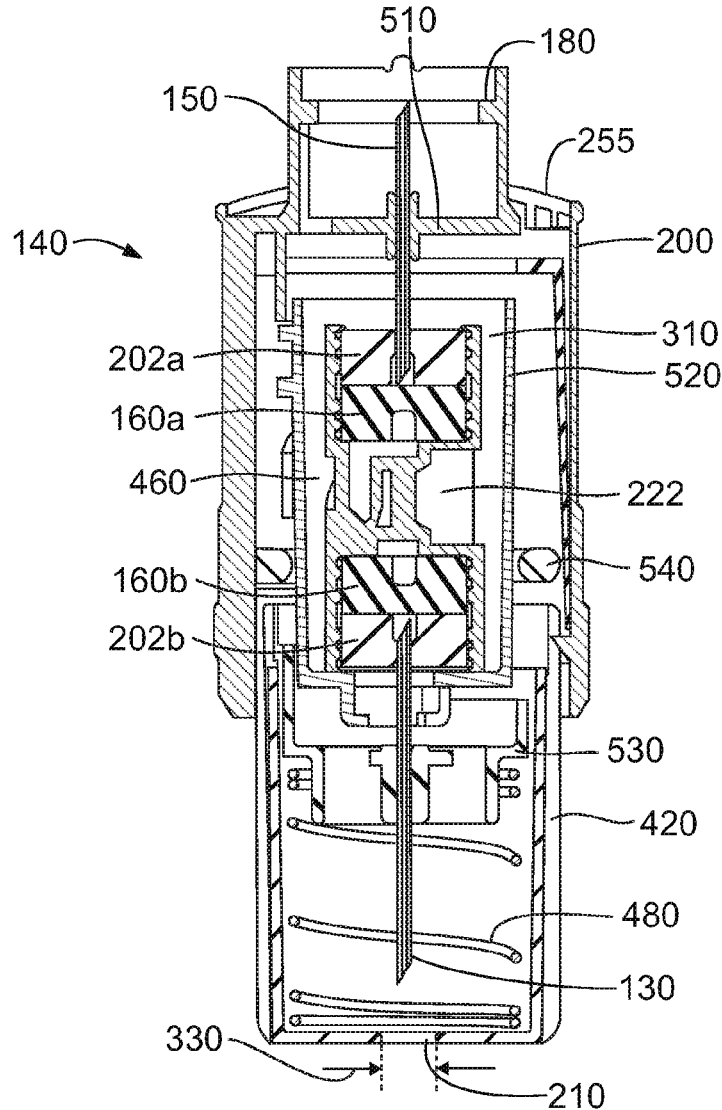
FIG. 9 is a sectioned view of the embodiment of the medicated module shown in FIG. 3 orientated in the bypass configuration.

One embodiment of the medicated module 140 of our invention is illustrated in FIGS. 3 and 9. In these embodiments the medicated module 140 contains a capsule 310 comprising a reservoir 222, two keepers 202a and 202b, and two seals 160a and 160b. Reservoir 222 contains a fixed single dose of a secondary medicament. In some cases this secondary medicament may be a mixture of two or more drug agents that can be the same or different from the primary drug compound in the drug delivery device 5. Preferably the capsule is permanently fixed within the medicated module, however, in some cases it may be preferred to design the module such that the capsule can be removed when empty and replaced with a new capsule.

In the embodiments shown in FIGS. 7 and 9, capsule 310 has ends that are sealed with pierceable membranes or septa 160a and 160b that provide a hermetically sealed and sterile reservoir 222 for the second medicament. A primary or proximal engagement needle 150 can be fixed in hub 510 connected to the proximal end of housing 200 of the module and configured to engage capsule 310 when needle guard is moving in the proximal direction during injection. The outlet, or distal needle 130, is preferably mounted in lower hub 530 and initially protrudes into lower keeper 202b. The proximal end of needle 130 pierces the lower septum 160b when the bypass housing 520 rotates and is moved proximally by the force exerted by needle guard 420 and spring 480 during injection.

When first attached to the auto-injector, the medicated module 140 is set at a pre-use or starting position. Preferably, indicator 410 shows through window 540 to inform the user of the pre-use condition of the medicated module. The indicator is preferably a color stripe or band on the outer surface of the proximal end of guard 420 (see FIG. 5) visible through an aperture in the outer body. The needle guard 420 is slidably engaged with inner surface of outer housing 200 by engagement of arms 120 and channels 100. Retention snaps 560 prevent the guard from disengaging the outer housing at its fully extended position. Housing 200 partially defines an internal cavity 21 that holds bypass housing 520, which contains capsule 310. A portion of the proximal end of housing 200 defines an upper hub 510 that holds needle 150. Optionally, as illustrated in FIG. 9, a shoulder cap 255 may be added to the proximal outer surface of outer housing 200. This shoulder cap can be configured to serve as indicia to identify to a user the type/strength of medicament contained in the module. The indicia can be tactile, textual, color, taste or smell.

FIG. 9 shows a cutaway or cross-sectioned view of the medicated module set in a pre-use or starting state where needles 130 and 150 are not piercing septa 160a and 160b. In this position, the bypass housing 520 is at its most extended position and needles 130 and 150 are not in fluid communication with medicament contained in capsule 310. The capsule is supported by bypass housing 520. In this neutral or suspended state of capsule 310, primary medicament 60 from the primary reservoir 70 in the cartridge holder 13 of auto-injector 5 can flow through needle 150 into keeper 202a, through bypass 460 and into keeper 202b, and eventually out through needle 130. This flow configuration allows a user to perform a priming step or procedure by administering a small dose of the primary medicament using the dosing mechanism 10 the drug delivery device 5.

The compression spring 480 is positioned between the distal end of bypass housing 520 and the inner proximal face of guard 420 to bias the guard 420 into an extended (guarded) position as illustrated in FIG. 9. Upon assembly, spring 480 is purposely compressed to supply a proximally directed biasing force against lower hub 530. This pre-compression of spring 480 is possible because the lower hub 530 and the bypass housing 520 are prevented from moving in an axial proximal direction by radial stand-off 400 located on the inside surface of the outer housing (FIG. 8) that engage with an upper stand-off pocket 660 and legs 270 of lower hub 530 engaging lower stand-off pocket 650. The combination of these stand-offs/legs and pockets prevent the lower hub and upper hub needles from piercing into the centre of the capsule until the device is triggered as previously described.

The proximal inside surface of guard 420 has one or more inwardly protruding features, drive teeth, pips, or like structures 220 that run in one or more tracks 230 or guide ways formed in the outer surface of bypass housing 520. As shown in FIG. 5, track 230 can be described as four paths, 290, 240, 250, and 260, that have a specific geometry such that after a single use of the medicated module 4 the drive tooth 220 is blocked from further axial movement and the guard (and device) is "locked" in a guarded position where the distal end of the needle is completely and safely covered by guard 420.

One unique feature of our medicated module assembly is the user feedback that is given when the assembly is used. In particular, the assembly could emit an audible and/or tactile "click" to indicate to the user that they have firstly triggered the device and secondly reached the "commit" point such that the needle guard will lock safely out upon completion of the injection/removal of the guard from the injection site. This audible and/or tactile feature could work as follows. As mentioned, the needle guard 420 is rotationally constrained by outer housing 200 and has one or more drive teeth 220 that are initially in path 290 of track 230 on bypass housing 520. As the guard is moved proximally, the spring 480 is further compressed exerting additional force in the proximal direction on lower hub 530, which is initially constrained axially by the lower stand-off pocket 650 engaged with legs 270. Likewise, the bypass housing 520 is constrained from moving proximally by upper stand-off pocket stop 732 engaged with stand-off 400 on the inner surface of outer housing 200. The drive teeth 220 travel in path 290 causing the bypass housing to rotate slightly. This rotation will disengage the upper stand-off 400 from upper standoff pocket stop 832, allows the drive teeth to enter path 240, and unblocks legs 270 from lower standoff pocket allowing the bypass housing to move proximally carrying with it capsule 310, where it then can engage needles 130 and 150. As the guard continues to move proximally, the drive teeth move from path 240 passed transition point 240a into path 250 causing further rotation of the bypass housing. As this rotation is completed the drive teeth transition to path 230, potentially emitting an audile "click" sound, as well as a tactile feel, to the user. This transition past point 250a (and the corresponding point directly below it on the track) constitute the "commit" point and as such, once it has been reached the needle guard 420 will "lock out" when it extends upon removal of the device from the injection site.

As mentioned, the distal end of the guard 420 has a planar surface 330 that provides an added measure of safety and reduces the pressure exerted by the guard on the injection site during an injection with our needle assembly. Because the planar surface 330 substantially covers access to needle 130 a user is prevented from gaining access to the distal tip of the needle after the assembly is in the locked position. Preferably, the diameter D of needle passing through hole 210 in the planar surface is no more than 10 times that of the outer diameter of needle cannula 130.

The outer proximal surface of the needle guard 420 preferably has indicia 410 that are preferably at least two different color stripes or bands, each of which is sequentially visible through the opening or window 540 in outer housing 200. One color could designate the pre-use or prime state of the module and the other color would indicate that the module is in finished or locked state, another color could be used to denote the transition through the trigger or "commit" point in case a user stops injection after trigger point but before "commit" point. For example, a green color could be the pre-use position and a band of red color could be used to indicate that the module has been used and is locked and an orange color could indicate that the device has been triggered but not locked out. Alternatively, graphics, symbols or text could be used in place of color to provide this visual information/feedback. Alternatively these colors could be displayed using the rotation of the bypass cavity and printed on or embedded into the bypass housing. They could be visible through the aperture by ensuring that he needle guard is made from a transparent material.

Figure 10:
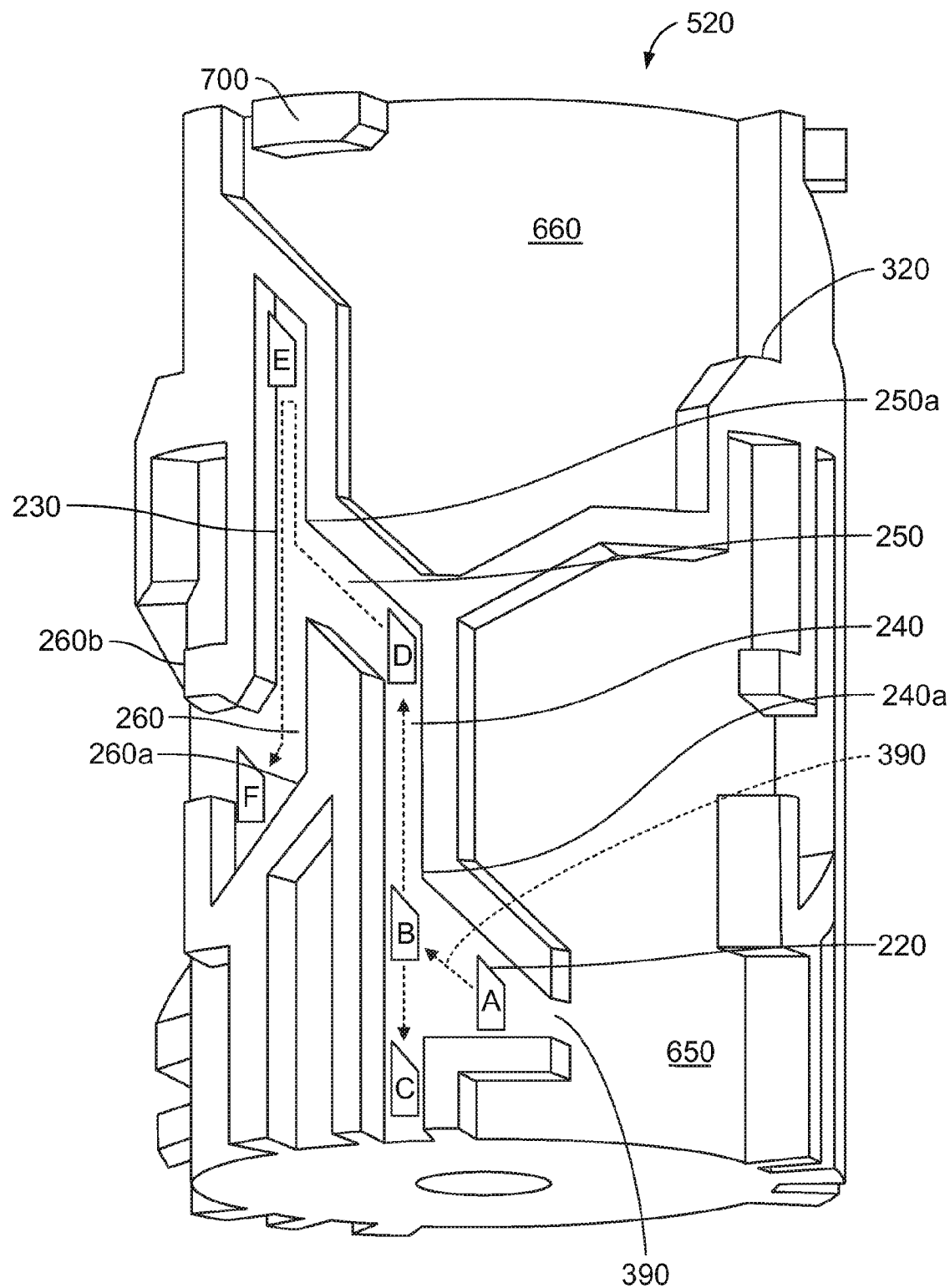
FIG. 10 is a close-up perspective view of the bypass housing of the embodiment of the medicated module shown in FIG. 2 to illustrate the positions of the drive tooth during use.

FIG. 10 illustrates the travel of drive teeth 220 in one or more tracks 230 as illustrated by directional arrow 390. Drive tooth 220 begins at position A and through axial movement of the needle guard biases the bypass housing rotationally until it moves past the transition point 240a and arrives at position B. Once the drive tooth reaches position B the bypass housing and lower needle hub move proximally causing the capsule 310 to engage needles 130 and 150, and the drive tooth moves relatively to position C (this is termed as the triggering of the device) and it is the bypass housing/lower hub moving proximally under the release of stored energy that results in the effective position of the needle guard drive tooth being position C. It is important to note that the needle guard does not move under the action of the release stored energy, it is just the needle hub and the bypass housing that move relatively away from the needle guard at the point of triggering, hence the drive tooth moves from position B to position C. As the needle guard continues to retract, drive tooth 220 moves proximally in path 240 to position D, where it exerts a rotational bias on the bypass housing 520 causing it to rotate again until tooth 220 passes the transition 250a (commit point) into path 260. The drive tooth then moves proximally until position E is reached. At this point, the needle guard 420 is fully retracted and the full available insertable length of the needle is exposed. Once the user removes the guard from contact with the skin, the guard begins to extend as a result of the distal biasing force exerted by spring 480 on the inner proximal surface of the guard. The utilization of the stored energy spring to act both as a trigger/piercing spring and also, once extended post triggering, as the needle guard spring is a unique aspect of this design. It negates the need to use two separate springs for these separate functions by locating the spring in a position such that it can fulfill both roles. Initially, for example during assembly or manufacture of the medicated module, the biasing member is compressed exerting a force on the lower hub/bypass housing in preparation for triggering. Once triggered it extends proximally where upon it can then be compressed from the distal end as the needle guard retracts against it. This secondary compression provides the force to push the needle guard back to the extended and locked position as it is removed from the injection site. As the guard moves to its fully extended post-use position, which preferably is less extended than the starting position, the drive tooth 220 moves distally in path 250 until it reaches transition point 260a, where it then rotationally biases the bypass housing 520 to rotate yet again until tooth 220 enters path 260 and arrives at position F. This last rotation of bypass housing 520 causes lock out boss 700 to engage lock out feature 710. This prevents any further rotational or axial movement of the bypass housing. The needle guard is prevented from further substantial axial movement, as defined earlier, by engagement of the drive tooth with axial stop 260b. It is within the scope of our invention that a number of tooth arrangements and/or profiles could be used to fulfill the required function described above, e.g., simple equal tooth profiles or more complex multi-angled profiles. The particular profile being dependent upon the required point of commit and rotation of the bypass housing. It is also within the scope of our invention that a similar axial/rotational locking of the lower needle hub to the bypass housing as of the bypass housing to the outer housing, could be integrated to prevent movement of the needle post-triggering and post-lock out.

In any of the above described embodiments of our invention the second medicament may be either in a powdered solid state, any fluid state contained within the secondary reservoir or capsule, or coated to the inside surface of the drug dispense interface. The greater concentration of the solid form of the medicament has the benefit of occupying a smaller volume than the liquid having lower concentration. This in turn reduces the ullage of the medicated module. An additional benefit is that the solid form of the second medicament is potentially more straightforward to seal in the secondary reservoir than a liquid form of the medicament. The device would be used in the same manner as the preferred embodiment with the second medicament being dissolved by the first medicament during dispense.

To minimize diffusion of the secondary medicament contained in the capsule within the medicated module into the primary medicament during dispense of the medicaments the reservoir 222 has an integral flow distributor 232. This flow distributor also ensures efficient expulsion of the second medicament from the system and greatly minimizes residual volume. One possible embodiment of the reservoir 222 and flow distributor 232 is illustrated in FIGS. 11 and 12. Preferably the reservoir and flow distributor are manufactured as a single part from materials that are compatible with the secondary medicament, most preferably as a single molded piece. A preferred material would be that typically used to manufacture septa or pistons (bungs) found in multi-dose medicament cartridges, although any material that is compatible with the medicament during long term storage would be equally applicable. The flow distributor 232 is configured and positioned in reservoir 222 such that the secondary medicament fills flow channels that are defined by the shape and location of one or more channels (not shown) inside the reservoir. The shape of the flow channels can be optimized for a plug flow of medicament by varying the dimensions of the flow distributor and/or channels. The cross-sectional area of the annulus formed between the flow distributor and the wall of the reservoir should be kept relatively small. The volume available to store the secondary medicament would equal the internal volume of the reservoir minus the volume of the flow distributor. Therefore if the volume of the flow distributor is marginally smaller than the internal volume of the capsule, a small volume is left which the secondary medicament occupies. Hence the scale of both the capsule and the flow distributor can be large while storing a small volume of medicament. Resultantly for small volumes of secondary medicament (e.g. 50 micro liters) the reservoir can be of an acceptable size for handling, transport, manufacture, filling and assembly.

As described above, in one arrangement, Applicants' medicated module comprises a needle guard. However, in an alternative arrangement, a medicated module may be provided without a needle guard. As just one example, and as illustrated in FIG. 13, an alternative medicated module is illustrated. This medicated module comprises screw threads as attachment means 808, however, any known attachment means can be used, including permanent and removable connection means. Threads, snap locks, snap fits, luer locks, bayonet, snap rings, keyed slots, and combinations of such connections can be used to attach module 804 to the auto-injector delivery device 807.

The medicated module 804 has the benefit of the second medicament 802 as a single dose being contained entirely within the cannula 803 hence minimizing the risk of material incompatibility between the second medicament and the materials used in the construction of the medicated module 4.

As shown in FIG. 13, a unique aspect of this embodiment is the method of construction of output needle 803, part of which has an enlarged cross-section 805 to accommodate the volume of the fixed (single) non-user settable dose medicament 802. Preferably a hydroforming or a swaging process will be utilized to form the enlarged cross-section 805 of the needle 803. Both tips of the needle are preferably not enlarged which is beneficial because it helps minimize both the physical and mental/emotional trauma associated with insertion of larger bore needles as well as minimizing the risk of compromising the sealing integrity of the septa of the primary medicament container (multiple piercing of this type of material with a relatively large gauge needle increases the risk of "coring" of the septum).

To minimize the residual volume of the second medicament that might remain in the needle module or sub-assembly 804 at the end of the dispense operation caused by recirculation, the enlarged section 805 should be designed with fluid flow characterizing models. Preferably, the design of medicated module 804 should ensure that at least about 80% of the second medicament is expelled through the distal end of needle 803, most preferably at least about 90% should be expelled. Ideally, displacement of the primary medicament 801 into the proximal end 806 of needle 803 will displace the second medicament 802 without substantial mixing of the two medicaments. Preferably this is accomplished by minimizing the diametric increase and careful design of the transition from the small cross sections of the needle 803 to the enlarged cross section 805. One alternative is to have the assembly/filling process set up so as to ensure that a "plug" of gas (e.g. air or an inert gas such as nitrogen) is present in the section 808 of the needle (above the enlarged section 805) this may act to ensure that the first and second medicaments are kept separate from each other thereby help ensure sequential delivery by action of a virtual piston created by the plug of air. This plug may additionally help ensure that there is no opportunity for the primary and secondary medicaments to mix prior to injection (i.e. if the medicated module is left in the attached position for an extended period of time prior to the injection action being undertaken.

Attachment of the medicated module 804 to the auto-injector delivery device 807 (such as the auto-injector 5 illustrated in FIG. 1A) causes the engagement needle 806 located in the module to penetrate the septum 810 of cartridge 812 of the auto-injector delivery device 807. Once the engagement needle 806 has passed through the septum of the cartridge, fluid connection is made between the first or primary medicament 801 and the output needle 803. The dose of the auto-injector device 807 is then set using a dose dial grip 7 (see FIG. 1A) in the normal manner (e.g., by dialing the appropriate number of units). Dispense of the medicaments is then achieved by subcutaneously injecting the medicaments via activation of the trigger slide 42 on auto-injector device 5 as previously described. In a preferred embodiment, the trigger slide 42 is operably connected to a piston rod that engages a piston in the primary reservoir of the first medicament.

Preferably the medicated module is provided by a drug manufacturer as a stand-alone and separate device that is sealed to preserve sterility. The sterile seal of the module is preferably designed to be opened automatically, e.g. by cutting, tearing or peeling, when the medicated module is advanced or attached to the drug delivery device by the user. Features such as angled surfaces on the end of the injection device or features inside the module may assist this opening of the seal.

The medicated module of our invention should be designed to operate in conjunction with a single use or a multiple use injection device. The injection device could be a reusable or disposable device. By disposable device it is meant an injection device that is obtained from the manufacturer preloaded with medicament and cannot be reloaded with new medicament after the initial medicament is exhausted.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A drug delivery system configured to deliver at least one liquid and at least one medicament comprising an auto-injector delivery device and a single dispense interface, the auto-injector delivery device comprising:
   a housing defining a primary reservoir, the primary reservoir containing a first liquid; and
   a dose setting mechanism operably connected to the primary reservoir to set a variable dose of the first liquid;
   the single dispense interface being configured for fluid communication with the primary reservoir of the auto-injector device; and
   the system further comprising a medicated module having a proximal end and a distal end, the medicated module comprising the single dispense interface at its distal end and a secondary reservoir containing at least one secondary medicament configured for fluid communication with the single dispense interface and the primary reservoir; the proximal end of the medicated module being configured to be releasably attachable to a distal end of the auto-injector delivery device wherein a single activation of the dose setting mechanism causes the first liquid from the primary reservoir and a non-user settable dose of the secondary medicament from the secondary reservoir to be expelled through the single dispense interface,
   wherein a single operation of the dose setting mechanism causes the first liquid from the primary reservoir to be expelled through the single dispense interface after at least substantially all of the non-user settable dose of the secondary medicament has been expelled through the single dispense interface.

2. The system of claim 1 wherein the primary reservoir contains at least one dose of a first medicament.

3. The system of any claim 1 wherein said secondary medicament comprises at least one of a GLP-1, a GLP-1 analog, and Insulin.

4. The system of claim 1 wherein the auto-injector delivery device further comprises a coupling mechanism for releasably coupling the medicated module to the auto-injector delivery device the coupling mechanism comprising at least one attachment means.

5. The system of claim 4 wherein the coupling mechanism comprises a first attachment means and a second attachment means, the first attachment means being different than the second attachment means.

6. The system of claim 4 wherein the coupling mechanism comprises a first attachment means and a second attachment means, the first attachment means having a first threaded section and a second attachment means having a second threaded section.

7. The system of claim 1 wherein the medicated module is configured to be disposable and replaceable with a replacement module comprising a new secondary reservoir and a new single dispense interface.

8. The system of claim 7 where the medicated module further comprises a needle guard, wherein the needle guard is operably connected to the secondary reservoir.

9. The system of claim 7, wherein the secondary reservoir is arranged within a bypass housing and the single dispense interface comprises a double ended needle cannula, wherein the medicated module further comprises at least one of the following features,
   a) an outer housing having an inner surface, a proximal end and a distal end, where the proximal end has an upper hub holding a first double-ended needle cannula and a connector configured for attachment to an auto-injector delivery device;
   b) the bypass housing having an outer surface and being slidably engaged with an upper radial stand-off on an inner surface of the housing;
   c) a reservoir within the bypass housing comprising a single dose of a medicament;
   d) a guard having an internal proximal face and a drive tooth on an inner surface, where the drive tooth is slidably engaged with a track on an outer surface of the bypass housing;
   e) a lower hub slidably engaged with an outer surface of the bypass housing and slidably engaged with an inner surface of the needle guard;
   f) a biasing member engaged between an internal proximal face of a guard and with a lower hub; and
   g) a lower hub holding a second double-ended needle cannula.

10. The system of claim 9 wherein the reservoir comprises a single molded component having an internal cavity with an integral flow distributor.

11. The system of claim 1 wherein the housing defining the primary reservoir comprises a cartridge holder and the auto-injector delivery device comprises at least one of the following features:
   a) the dose setting mechanism being operably connected to the cartridge holder containing the first medicament containing at least one drug agent;
   b) a biasing member operatively coupled to the dose setting mechanism;
   c) a dose dial grip operably coupled to the dose setting mechanism and to a biasing member, the dose dial grip being moveable to a selected set position against a bias of the biasing member, wherein movement of the dose dial grip to the selected position is accompanied by straining the biasing member; and
   d) a trigger on the dose setting mechanism arranged to retain a dose dial grip in the set position against a bias of the biasing member.

12. The system of claim 11 wherein the auto-injector delivery device comprises a coupling mechanism for releasably coupling the secondary reservoir to the auto-injector delivery device.

* * * * *